United States Patent [19]

Frame et al.

[11] Patent Number: 4,737,479
[45] Date of Patent: Apr. 12, 1988

[54] PROCESS FOR THE OLIGOMERIZATION OF OLEFINS AND A CATALYST THEREOF

[75] Inventors: Robert R. Frame, Glenview; Paul T. Barger, Arlington Heights, both of Ill.

[73] Assignee: UOP Inc., Des Plaines, Ill.

[21] Appl. No.: 25,535

[22] Filed: Mar. 13, 1987

Related U.S. Application Data

[63] Continuation-in-part of Ser. No. 842,689, Mar. 21, 1986, abandoned.

[51] Int. Cl.$^4$ ................................................ C07C 2/30
[52] U.S. Cl. .................................... 502/117; 585/512; 585/521; 585/531
[58] Field of Search ................ 502/117; 585/512, 521, 585/531

[56] References Cited

U.S. PATENT DOCUMENTS 3,155,642  11/1964  Duck et al. ................ 260/94.3
3,457,321   7/1969  Hambling et al. .......... 260/683.15

FOREIGN PATENT DOCUMENTS 47-22206  6/1972  Japan .
50-24282  8/1975  Japan .

Primary Examiner—Asok Pal
Attorney, Agent, or Firm—Thomas K. McBride; John F. Spears, Jr.; Raymond H. Nelson

[57] ABSTRACT

An olefinic feedstock containing contaminants such as oxygenates may be oligomerized to a desired oligomer which contains a particular configuration. The process may be effected by utilizing a catalyst which comprises a porous support containing a catalytically effective amount of a non-stoichiometric hydrogen and oxygen-containing iron group metal compound in combination with a catalytically effective amount of an alkyl aluminum compound and an activator comprising an aluminum alkoxide. The presence of the latter compound in the catalyst compound will permit the catalyst to maintain its activity and stability over a relatively long period of time.

15 Claims, No Drawings

PROCESS FOR THE OLIGOMERIZATION OF OLEFINS AND A CATALYST THEREOF

CROSS-REFERENCE TO RELATED APPLICATION

This application is a continuation-in-part application of our copending application Ser. No. 842,689 filed Mar. 21, 1986, all teachings of which are incorporated herein by reference thereto, now abandoned.

BACKGROUND OF THE INVENTION

The oligomerization of olefins is known in the art, such oligomerization processes being effected by treating olefinic hydrocarbons with certain catalysts to obtain various oligomers which will find a useful function in the chemical art. One type of catalyst which may be employed for this particular type of reaction comprises a supported metal compound. For example, U.S. Pat. No. 3,562,351 discloses a method for dimerizing olefins utilizing a supported catalyst which has been prepared by impregnating a suitable support with a salt solution of a Group VIII metal followed by a heat treatment in an inert atmosphere at a temperature less than that which is required to form a metal oxide but which will form a complex on the surface of the solid support. Following this, the catalyst is activated by treatment with an organometallic compound. U.S. Pat. No. 3,483,269 describes a catalyst useful for oligomerizing lower olefins which comprises a π-allyl nickel halide supported on an acidic inorganic oxide support. If so desired, the support may have been optionally treated with an alkyl aluminum compound. U.S. Pat. No. 3,592,869 also describes a catalyst which is useful for the oligomerization of olefins. A divalent nickel compound and an alkyl aluminum compound are contacted with an olefinic compound. The resulting mixture is then used to impregnate an inorganic refractory oxide support. Another patent, namely U.S. Pat. No. 3,644,564, describes a catalyst for the oligomerization of ethylene which comprises an organo aluminum-free reaction product of a nickel compound which is an atom of nickel in complex with an olefinically unsaturated compound and a fluorine-containing ligand. The catalysts are typically formed in situ. U.S. Pat. No. 3,679,772 describes a process for reacting monoolefins with diolefins, the catalyst for such a reaction comprising a complex of (1) nickel, (2) a Group VA electron donor ligand such as an organophosphine, (3) a nonprotonic Lewis acid and (4) a reducing agent which itself may be a Lewis acid, all of which are composited on an acidic silica-based support.

U.S. Pat. No. 3,697,617 describes an oligomerization process involving the use of a catalyst comprising a complex of nickel with a chloro-containing electron donor ligand such as chlorodiphenylphosphine combined with a nonprotonic Lewis acid which is capable of forming a coordination bond with nickel and a reducing agent capable of reducing nickel acetylacetonate to an oxidation state less than 2. This complex may be composited on a solid support comprising an acidic silica-based material such as silica-alumina. The Lewis acid and the reducing agent may comprise the same compound as, for example, ethyl aluminum sesquichloride. U.S. Pat. No. 3,663,451 describes a catalyst which is obtained by reacting a transition metal halide such as nickel halide with a carrier to give a carrier-metal bond. This product is then reacted with a ligand such as a phosphine or ketone and finally activated by treatment with an aluminum alkyl or chloro alkyl.

U.S. Pat. No. 3,755,490 describes the polymerization of an olefin utilizing a catalyst comprising nickel, a Group VA electron donor ligand, a Lewis acid, and a reducing agent on a solid acidic silica-based support. U.S. Pat. No. 3,954,668 is drawn to an oligomerization catalyst comprising a nickel compound, a chloro-containing electron donor ligand, or a phosphorous compound, a nonprotonic Lewis acid reducing agent which is capable of reducing nickel acetylacetonate to an oxidation state of less than 2 and which is also capable of forming a coordination bond with a nickel. U.S. Pat. No. 3,170,904 speaks to a catalyst which is useful for polymerization comprising a large surface area metal of Groups VIIA or VIII of the Periodic Table, boron trifluoride etherate, an organometallic compound of Groups I, II, III or IV or a halo derivative of an organometallic compound of Groups II, III or IV or a hydride of a metal of Groups I, II or III. The large surface area metal which comprises one component of this catalyst is in metallic form as, for example, Raney nickel. If so desired, the catalyst may be composited on a diatomaceous earth carrier. In like manner, U.S. Pat. No. 3,170,906 discloses a catalyst which comprises (A) a carrier-supported nickel or cobalt oxide which has been prepared by impregnating the carrier with the hydroxide, organic acid salt, inorganic acid salt, followed by oxidation in the presence of oxygen or a combination of nitrogen and oxygen; (B) a boron, titanium, zirconium, or vanadium halide; and (C) an alkyl metal or alkyl metal halide. In addition to these patents, British Pat. No. 1,390,530 describes an oligomerization catalyst which has been prepared by thermally pretreating a metal oxide carrier material followed by reacting with a halogen-containing organoaluminum compound and thereafter in a step-wise fashion, impregnating this product with a divalent nickel or cobalt complex at temperatures ranging from −50° to 150° C.

Several other patents which describe oligomerization or polymerization catalysts which are unsupported in nature or processes include Japanese Pat. No. 5024282 which is drawn to a catalyst containing a Group VIII metal and tin chloride or zinc chloride as well as Japanese Pat. No. 4722206 which describes an unsupported catalyst prepared by mixing a nickel compound, an aluminum organic compound and a tin tetrahalide. U.S. Pat. No. 3,155,642 describes an unsupported catalyst prepared from an alkyl tin compound and aluminum chloride in addition to a nickel or cobalt compound for the polymerization of a dienic compound. U.S. Pat. No. 3,155,642 also describes an unsupported catalyst comprising a nickel carboxylate, a halide of a metal of Group IV or V and an organoaluminum compound containing at least one alkoxy radical, said catalyst being used for the polymerization of cis-1,4- polybutadiene. Likewise, U.S. Pat. No. 3,457,321 describes an unsupported catalyst prepared from a complex organic compound of a metal of Group VIII, a reducing agent and a tin tetraalkyl compound. Furthermore, U.S. Pat. Nos. 3,483,268 and 3,505,425 are also drawn to unsupported catalysts, the former showing a catalyst comprising nickel acetyl acetonate, an organonickel compound, and an activating agent of an aluminum alkyl alkoxide or aluminum trialkyl while the latter is drawn to a process for preparing this catalyst. British Pat. No. 1,123,474 likewise teaches a process for preparing linear dimers using a catalyst comprising a complex organic compound of a metal of a Group VIII and a tin tetraalkyl compound.

It is to be noted again that each of the patents discussed in the above paragraph are drawn to unsupported catalysts for use in dimerization or polymerization reactions using different starting materials in the preparation thereof in contradistinction to the supported catalyst of the present invention which is hereinafter more fully described as to composition and method of preparation as well as the use thereof.

As will hereinafter be shown in greater detail, the oligomerization of olefinic hydrocarbons to provide products which possess a desired configuration with respect to the branching or minimal branching of the resultant chain may be accomplished by treating said olefins in the presence of a catalyst of the present invention, this catalyst will maintain its activity and stability for a relatively long period of time in the presence of certain impurities or poisons in the feedstock.

BRIEF SUMMARY OF THE INVENTION

This invention relates to a catalytic composite which is useful for the oligomerization of olefinic hydrocarbons. More specifically, the invention is concerned with a catalyst composite and a process for the oligomerization of olefinic compounds, particularly olefinic hydrocarbons, whereby the use of the catalytic composite will result in the obtention of selective oligomers of the olefinic feed stock.

The term "polymerization" has a relatively broad meaning in the chemical art. Although it is generally referred to as the preparation of relatively high molecular weight polymers, that is polymers possessing molecular weights of greater than 50,000 or more, it may also refer to low molecular weight polymers, that is, polymers possessing molecular weights lower than 50,000. In contradistinction to this, the term "oligomerization" refers to polymeric compounds in which the molecules consist of only a relatively few monomeric units and thus would include dimerization, trimerization or tetramerization.

Many olefinic hydrocarbons which contain from 4 to about 12 carbon atoms in the chain are utilized in various industries in many ways. For example, dimers of propylene regardless of the amount of branching may be used to improve the octane number of motor fuels which are utilized in internal combustion engines utilizing gasoline as the fuel thereof. The presence of these compounds in a motor fuel such as gasoline will improve the octane number of the fuel to a high level, thus enabling the gasoline to be utilized in combustion engines in an unleaded state. Other uses for dimers containing 6 carbon atoms would be in the synthesis of flavors, perfumes, medicines, dyes and resins. Another use of an oligomer would be found in the dimerization product of butene in which the dimer which possesses a relatively straight chain configuration with a minimum of branching such as one methyl substituent on the chain would be as an intermediate in the production of a plasticizer. The plasticizer, when added to a plastic will facilitate compounding and improve the flexibility as well as other properties of the finished product. Likewise, a trimer of butene or a dimer of hexane in which the olefin contains 12 carbon atoms may be used as an intermediate in various organic syntheses such as in the preparation of detergents, lubricants, additives, plasticizers, flavors, perfumes, medicines, oil, dyes, etc. In addition, linearized oligomers containing 12 or more carbon atoms, upon hydrogenation, provide excellent diesel fuels.

It is therefore an object of this invention to provide a catalyst for the oligomerization of olefinic hydrocarbons.

A further object of this invention is to provide a specific catalyst system which may be used in a process for the oligomerization of olefinic hydrocarbons whereby selective oligomers may be obtained as a result of this process.

In one aspect an embodiment of this invention resides in a catalytic composite comprising a combination of a catalytically effective amount of an alkyl aluminum compound and a catalytically effective amount of an activator comprising an aluminum alkoxy compound composited on a porous support containing a catalytically effective amount of a non-stoichiometric hydrogen and oxygen-containing iron group metal compound.

Another embodiment of this invention is found in a process for the oligomerization of an olefinic hydrocarbon which comprises treating said olefinic hydrocarbon at oligomerization conditions in the presence of a catalytic composite comprising a catalytically effective amount of an alkyl aluminum compound and a catalytically effective amount of an activator comprising an aluminum alkoxy compound composited on a porous support containing a catalytically effective amount of a non-stoichiometric hydrogen and oxygen-containing iron group metal compound, and recovering the resultant oligomer.

A specific embodiment of this invention is found in a catalytic composite comprising a combination of a catalytically effective amount of nickel hydrate plus an activator comprising catalytically effective amounts of diethyl aluminum chloride and tri-t-butoxy aluminum composited on an alumina support.

Another specific embodiment of this invention is found in the process for the oligomerization of an olefinic hydrocarbon which comprises treating propylene in the presence of a catalyst comprising a combination of a catalytically effective amount of nickel hydrate, and catalytically effective amounts of diethyl aluminum chloride and tri-t-butoxy aluminum at a temperature in the range of from about $-20°$ to about $120°$ C. and a pressure in the range of from about 350 to about 1,000 pounds per square inch gauge, and recovering the resultant oligomer comprising a mixture of hexene, methylpentene and dimethylbutene.

Other objects and embodiments will be found in the following detailed description of the invention.

DETAILED DESCRIPTION OF THE INVENTION

As hereinbefore set forth, the present invention is concerned with a catalyst composite which may be utilized for the oligomerization of olefins and to a process which employs the catalyst. Heretofore, the preparation of a catalytic composite which may be used for the polymerization or oligomerization of olefinic compounds was relatively difficult inasmuch as several relatively expensive compounds were required as components of the composite, as well as entailing somewhat complicated methods for the manufacture thereof. In contradistinction to this, the catalytic composite of the present invention is relatively easy to prepare and, in addition, employs compounds which are less expensive than the components of the other catalyst. The final catalytic composite of the present invention will possess a high activity and will be stable over a relatively long period of time. Furthermore, the catalytic composite of the present invention will possess the desired stability and activity due to the ability of the catalyst to effect the desired oligomer reaction in spite of the presence of impurities which would, under ordinary circumstances, poison or deactivate the catalyst.

The particular impurities which are present in the feedstock, usually in an amount of from about 0.1 wt. ppm to about 100 wt. ppm, may be generically termed "oxygenates". The oxygenates will include such oxygen-containing organic compounds as alcohols, ethers, aldehydes and ketones. Some specific examples of these will include lower molecular weight alcohols such as methyl alcohol, ethyl alcohol, propyl alcohol, isopropyl alcohol, n-butyl alcohol, sec-butyl alcohol, t-butyl alcohol, etc.; ethers such as dimethyl ether, diethyl ether, dipropyl ether, methyl ethyl ether, methyl t-butyl ether, ethyl propyl ether; aldehydes such as formaldehyde, acetylaldehyde, etc.; and ketones such as acetone, methyl ethyl ketone, methyl propyl ketone, etc. These impurities which are generally present in trace amounts such as in a range of from about 0.1 to about 100 ppm will, in most instances, have a deleterious effect on the activity and stability of catalyst systems which have heretofore been employed to effect an oligomerization of olefinic hydrocarbons and thus quickly deactivate the catalyst when these impurities are present.

However, in contradistinction to the loss of activity or stability which has been exhibited by prior catalysts, we have now unexpectedly discovered that the novel catalysts of the present invention which have been prepared according to the method herein set forth, exhibit an unexpected resistance to the poisoning effect of the impurities and thus, will maintain a desired activity as well as remaining stable for a long period of time when employed in the conversion of olefinic hydrocarbons of the type hereinafter set forth in greater detail to form the desired products. In addition to these desired attributes, the catalyst will also produce a high yield of dimer products, especially from $C_3$ and $C_4$ olefins as compared to trimer and tetramer products. The dimer products produced by the oligomerization of propylene or the n-butenes will possess a high percentage of linear compounds, that is, n-hexenes and n-octenes and also a high percentage of dimers which contain only one methyl substituent; more highly branched oligomers being minority products. The propylene dimers which are produced by the process of the present invention all possess high octane numbers regardless of the branching, and thus are excellent octane blending components. In addition, the n-butene dimers are excellent as intermediates in the preparation of plasticizers.

The catalytic composite of the present invention will comprise a combination of a catalytically effective amount of a hydrate of an iron group metal salt and catalytically effective amount of an alkyl aluminum compound plus a catalytically effective amount of an activator comprising an aluminum alkoxy compound composited on a porous support. In the preferred embodiment of the invention, the iron group metal hydrate will be obtained from a soluble salt of nickel or cobalt such as, for example, nickel nitrate, nickel hydroxide, nickel bromide, nickel chloride, nickel fluoride, nickel acetate, cobaltic chloride, cobaltous acetate, cobaltous ammonium chloride, cobaltous bromide, cobaltous fluoride, cobaltous perchlorate, cobaltous sulfate, etc. The porous support upon which the iron group metal hydrate is impregnated will include inorganic metal oxides such as alumina, silica, mixtures of oxides such as alumina-silica, alumina-zirconia-magnesia, etc. or crystalline aluminosilicates which are commonly known as zeolites.

The second component of the catalyst composite will comprise alkyl aluminum compounds such as dimethyl aluminum chloride, diethyl aluminum chloride, dipropyl aluminum chloride, dimethyl aluminum bromide, diethyl aluminum bromide, dipropyl aluminum bromide, dimethyl aluminum iodide, diethyl aluminum iodide, dipropyl aluminum iodide, etc.

The third component of the catalyst composite will comprise an aluminum alkoxy component which will act as an activator for the catalytic composite. Examples of these aluminum alkoxy compounds will possess the generic formula $Al(OR)_3$ in which R comprises a lower molecular weight alkyl radical containing from one to about six carbon atoms. Some specific examples of these aluminum alkoxy compounds will include trimethoxy aluminum, triethoxy aluminum, tripropoxy aluminum, triisopropoxy aluminum, tri-n-butoxy aluminum, tri-t-butoxy aluminum, tripentoxy aluminum, trihexoxy aluminum, etc. It is also contemplated within the scope of this invention that the catalytic composite may, if so desired, also contain an aluminum halide such as aluminum chloride, aluminum bromide, aluminum iodide, etc. It is to be understood that the aforementioned list of iron group metal compounds, alkyl aluminum compounds, aluminum alkoxy compounds and porous supports are only representative of a class of compounds which may be employed to form the catalytic composite of the present invention, and that said invention is not necessarily limited thereto.

The oligomerization catalyst of the present invention may be prepared in such a manner so as to provide the finished catalyst with certain characteristics with regard to the selectivity of olefins obtained by the reaction of an olefin in the presence of said catalyst as well as a specificity of the product so obtained. The catalyst composite is prepared by impregnating a porous support of the type hereinbefore set forth with a simple divalent iron group metal salt such as, for example, nickel nitrate, preferably from an aqueous solution. After impregnation of the porous support such as alumina, which is effected at ambient temperature and atmospheric pressure, the impregnated support is then subjected to a thermal treatment. By varying the temperature of the thermal treatment, it is possible to obtain a catalyst composite which will provide a greater selectivity to dimer products resulting from the oligomerization of the olefin in contrast to trimer and tetramer products than are obtained when using other conventional oligomerization catalysts. The thermal treatment of the impregnated support is preferably effected in a range of from about 300° C. to about 450° C., the preferred thermal treatment temperature being in a range of from about 340° C. to about 360° C. The thermal treatment or calcination of the catalyst base containing the impregnated iron group metal salt in hydrate form will result in a weight loss due to a loss of water of hydration from the metal salt and will result in the formation of a non-stoichiometric hydrogen and oxygen-containing iron group metal compound which also may be referred to as a hydrate of an iron group metal salt. In the preferred embodiment of the invention, the mole ratio of water of hydration to iron group metal following the thermal treatment will be greater than 0.5:1 and preferably in a range of from about 0.5:1 to about 6:1. The thermal treatment of the catalyst base containing the iron group metal compound in the form of a hydrate will usually be effected for a period of time which is less than that required to completely drive off all of the water of hydration.

The thermal treatment or calcination of the catalyst base and the iron group metal salt at temperatures within the range hereinbefore set forth will result in a bonding of the iron group metal to the catalyst base usually by means of a metal-oxygen-base bond, the oxygen portion of the bond being supplied in part by the hydroxyl groups which are present on the surface of the porous support of the type hereinbefore set forth in greater detail.

Following the thermal treatment, the iron group metal impregnated catalyst base is then treated with an alkyl aluminum compound and an aluminum alkoxy compound to produce a catalyst of maximum activity. The treatment of the base with the aluminum alkyl compound and the activator is also effected at ambient temperature and atmospheric pressure utilizing a solution of the two compounds dissolved in an organic solvent such as benzene, toluene, isomeric xylenes, etc. In the preferred embodiment of the invention, in addition to the alkyl aluminum compound which may be of the type hereinbefore set forth in greater detail, an aluminum halide compound may also be used in this step. The addition of the organic solution, or conversely the addition of the impregnated base to the organic solution, will result in an exothermic reaction and after thorough admixture, the solution is allowed to return to room temperature. The solvent may then be removed by conventional means such as decantation, evaporation, etc. and the catalyst thereafter washed with an organic solvent to remove residue or trace portions of unwanted compounds. Thereafter, the catalyst may then be dried by purging with nitrogen, and recovered. In the finished composite, the alkyl aluminum compound is present in the composite in a mole ratio in the range of from about 0.05:1 to about 6:1, preferably in a range of from about 0.1:1 to about 1:1, moles of alkyl aluminum compound per mole of iron group metal, the latter being present in said composite, on an elemental basis, in an amount in the range of from about 1% to about 20% by weight of the composite, and preferably in an amount in a range of from about 1% to about 10%.

As will hereinafter be shown in greater detail, by preparing a catalyst which possesses the various components in the finished composite in mole ratios or weight percent within the ranges hereinbefore set forth, it is possible to selectively oligomerize olefin compounds containing from about 2 to about 6 carbon atoms with a concurrent obtention of desirable isomers in each of the oligomer products. In addition, by utilizing an aluminum alkoxide as a component of the catalyst composite in addition to the alkyl aluminum compound, it is possible to obtain a catalyst composite which will be more stable and more active in the conversion of olefins to oligomers than are catalysts which do not contain this compound.

As an example of how the catalyst composite of the present invention may be prepared, a predetermined amount of a porous base such as alumina, silica, silica-alumina, aluminosilicate, etc. which may be in the form of spheres, pellets, rods, etc. may be placed in an appropriate apparatus such as an evaporator along with an aqueous solution of a hydrate of an iron group metal salt. The mixture may be thoroughly admixed and following this, the apparatus heated to form the desired iron group metal impregnated base. The impregnated base may then be placed in a heating apparatus such as a tube furnace and treated with air while bringing the catalyst to a temperature of about 250° C. The heating is accomplished at a relatively slow rate and after the determined temperature has been reached, it is maintained thereat for an additional period of time which may range from about 2 to about 4 hours or more in duration. The calcination of the catalyst base is then effected by increasing the temperature to a predetermined level and maintaining thereat for a period of time sufficient to bring the mole ratio of water of hydration present in the iron group metal salt to a determined level which is preferably in an excess of about 0.5:1 moles of water of hydration per mole of iron group metal.

After allowing the calcination to proceed for this predetermined period of time, heating is discontinued and the catalyst base which contains from about 1% to about 20% by weight of iron group metal is allowed to cool. The cooled base may then be admixed with a solution of an alkyl aluminum compound and an aluminum alkoxy compound dissolved in an organic solvent. As previously discussed, the resulting reaction is exothermic in nature and after allowing the heat to dissipate, the resulting admixture is thoroughly stirred and allowed to stand for a period of time which may range from about 1 to about 100 hours or more in duration. At the end of this period, the organic solvent is removed by decantation, filtration, centrifugation, etc. and the solid catalyst is washed to remove any unreacted material. After washing, the catalyst is then dried in an inert atmosphere such as that provided for by the presence of nitrogen, and recovered.

The oligomerization of olefins containing from 2 to about 6 carbon atoms such as ethylene, propylene, butene-1, butene-2, pentene-1, pentene-2, pentene-3 may then be effected by treating the oligomer in the presence of the catalyst at oligomerization conditions which will include a temperature in the range of from about −20° to about 120° C., the preferred range being from about 30° to about 80° C., and a pressure in the range of from about 350 to about 1,000 per square inch gauge (psig). The pressure which is utilized may be the autogenous pressure provided for by the feedstock, if in gaseous phase, or, the feedstock may supply only a partial pressure, the remainder of said pressure being provided by the introduction of an inert gas such as nitrogen, helium, argon, etc. into the reaction zone.

It is contemplated within the scope of this invention that the oligomerization process may be effected in either a batch or continuous type operation. For example, when a batch type operation is employed, a quantity of the novel catalyst composite of the present invention may be placed in an appropriate apparatus such as, for example, an autoclave of the rotating, mixing or stirring type. If the olefinic feedstock is in gaseous form, the autoclave is sealed and the feedstock comprising the olefinic hydrocarbon or a mixture of olefinic and paraffinic hydrocarbon or similar carbon atom length are charged to the reactor until the desired operating pressure has been attained. The apparatus is then heated to the desired operating temperature and maintained thereat for a predetermined period of time which may range from about 1 to about 6 hours or more in duration. At the end of this period of time, heating is discontinued and after the apparatus and contents thereof have returned to room temperature, the excess pressure is discharged and the autoclave is opened. The reaction product is recovered, separated from the catalyst by conventional means such as decantation, filtration, centrifugation, etc. and, if so desired, subjected to fractional distillation whereby the various isomers may be separated, one from another, and stored. Conversely, if so desired, the reaction product comprising a mixture of isomers may be recovered and stored per se without separating the various isomeric fractions which are present in the product mixture.

In the event that the olefinic charge stock is in liquid form, it may be charged to the reactor which is thereafter sealed and pressured to the desired operating pressure by the introduction of an inert gas of the type hereinbefore set forth. The remainder of the operating pressure to obtain the desired oligomer product is carried out in a manner similar to that previously described.

When utilizing a continuous method of operation to obtain the desired oligomer products, a quantity of the catalyst composite is placed in an appropriate reactor. The feedstock comprising the olefinic compound is continuously charged to this reactor which is maintained at the proper operating conditions of temperature and pressure. As in the case of the batch type operation, the desired operating pressure may be provided for by the olefinic hydrocarbon itself or by the addition of a heated inert gas. After passage through the reactor for a predetermined period of time, the reactor effluent is continuously discharged and the reaction product may be recovered and passed to storage or it may be passed to a distillation apparatus whereby separation of the various isomers and oligomers may be effected. Any unreacted olefinic hydrocarbon which is recovered from the reactor effluent may be recycled back to the reactor to form a portion of the feed charge.

Inasmuch as the catalyst composite of the present invention is in solid form, the continuous method of operation for obtaining the desired oligomers of the olefinic hydrocarbons may be effected in various types of operations. For example, in one type of operation, the catalyst is positioned as a fixed bed in the reaction zone and the olefinic feedstock is charged so that it passes over the catalyst bed in either an upward or downward flow. Another type of continuous operation which may be employed comprises the moving bed type of operation in which the catalyst bed and the feedstock are passed through the reaction zone either concurrently or countercurrently to each other. In addition to the fixed or moving bed type of operation, it is also contemplated that the slurry type of operation may be employed, especially when the olefinic hydrocarbon feedstock is in liquid form. When this type of operation is employed, the catalyst is charged to the reactor as a slurry in the olefinic feedstock.

Examples of oligomers of olefinic compounds which may be obtained when utilizing the catalyst composite of the present invention will include n-butene, isobutene, n-hexene, methyl pentene, dimethyl butene, n-octene, the isomeric methyl heptenes, dimethyl hexenes, n-dodecene, the isomeric methyl undecenes, dimethyl decenes, etc. As was previously stated, the oligomer products which are obtained in the process of this invention will comprise, in the main, the dimers of the particular olefinic compound which was employed as the feedstock, thus, for example, when employing ethylene as the feed, the reaction product will comprise mostly $C_4$ olefins; when employing propylene as the feedstock, the reaction product will comprise mostly $C_6$ olefins; and when employing butene as the feedstock, the reaction product will comprise mostly $C_8$ olefins. Thus, the catalyst composite of the present invention will result in products which find particular uses in the finished product.

The following examples are given for purposes of illustrating the novel catalyst composites of the present invention, methods for preparing these composites and a process for utilizing these composites. However, it is to be understood that these examples are merely illustrative in nature and that the present invention is not necessarily limited thereto.

EXAMPLE I

A catalyst of the present invention was prepared by impregnating 250 cc of alumina spheres with an aqueous solution of nickel nitrate hexahydrate. The impregnation was effected in a rotary evaporator in which the mixture was rolled for a period of 0.5 hours with no heat. The evaporator was then heated with steam for a period of two hours during which time the water phase was evaporated. Following this, the catalyst base, comprising the nickel nitrate containing alumina, was loaded into a tube furnace and air was passed through the catalyst bed at a rate of 600 cc per minute. The temperature of the bed was then raised to 250° C. during a period of two hours and thereafter the bed was maintained at this temperature for an additional period of three hours. The temperature was then increased to 400° C. and maintained at this temperature for a period of two hours. Following this, heating was discontinued and the impregnated base was recovered. It contained 5.56 wt. % nickel.

The catalyst was then activated by adding a two-phase solution prepared by mixing 2.9 grams of tri-t-butoxy- aluminum with a toluene solution of 7.3 grams of diethyl aluminum chloride per 100 cc of supported nickel catalyst. The addition of the solutions was accomplished in a glove box while maintaining a nitrogen atmosphere. After thorough admixture, the solution was allowed to stand for a period of 12 hours with intermittent swirling thereof. The addition of the activator solution which was effected during a 15 minute period resulted in the evolvement of heat due to the exothermic nature of the reaction. At the end of the 12 hour period, the solvents were decanted and the catalyst was washed with six portions of isopentane utilizing 100 to 115 cc per wash. The resulting catalyst composite was then allowed to dry by evaporation of the excess isopentane in a glove box in a nitrogen atmosphere until it became free-flowing. The finished catalyst contained 4.90 wt. % of nickel and 5.60 wt. % of chlorine.

EXAMPLE II

A second catalyst composite was prepared in a manner similar to that set forth in Example I above. The catalyst base comprising 250 cc of alumina was impregnated with an aqueous solution of nickel nitrate hexahydrate and calcined in a stream of air at a temperature of 250° C. for a period of three hours and at a temperature of 400° C. for a period of two hours. The impregnated base, at the end of this time, contained 5.43 wt. % nickel.

The activation of the catalyst base was effected by treating the base in a toluene medium, by the addition of a solution prepared from 2.17 grams of t-butyl alcohol, 1.34 grams of triethyl aluminum and 7.25 grams of diethyl aluminum chloride per 100 cc of support. As in the previous example, the solution was slowly added during a period of 15 minutes to prevent overheating of the catalyst due to the evolvement of heat involved in the exothermic reaction. After allowing the solutions to stand for a period of 12 hours, the impregnation liquors were decanted and the solid catalyst was washed with six portions of isopentane. This catalyst was then allowed to dry in a glove box under nitrogen until it was free-flowing in nature.

EXAMPLE III

In this example, a third catalyst was prepared by impregnating alumina spheres with an aqueous solution of nickel nitrate hexahydrate in a steam-jacketed rotary evaporator. The impregnation was effected in a manner set forth in Example I above and, after evaporation of the water phase, the catalyst base was recovered and calcined in a tube furnace at a temperature of 250° C. for a period of three hours and at a temperature of 400° C. for a period of two hours. The finished catalyst base contained 5.6 wt. % of nickel after calcination.

The catalyst base was then activated with a toluene solution of 1.5 grams of aluminum chloride and 7.3 grams of diethyl aluminum chloride per 100 cc of support. The support was placed in a glove box covered with toluene and the activator solution was slowly added during a 15 minute period, during which time heat was evolved due to the exothermic nature of the reaction. As in the previous experiments, the addition of the activating solution was accomplished in a nitrogen atmosphere. The flask was intermittently swirled over a period of 12 hours following which the solvents were decanted and the catalyst was washed with six portions of isopentane. The catalyst was dried in a glove box under a nitrogen atmosphere until all of the excess pentane was evaporated and the catalyst became free-flowing in nature.

EXAMPLE IV

The catalyst which was prepared according to the method set forth in Example I above was utilized in the oligomerization of a n-butene feed. The oligomerization was effected by placing 50 cc of the catalyst in a tubular reactor having a ½" inner diameter, the length of the catalyst bed being 13.75". The feedstock, comprising a mixture of 60% n-butenes and 40% n-butane, which also contained about 60 ppm of a contaminant comprising methyl-t-butyl ether, was charged to the reactor at a LHSV of 2.0 hrs$^{-1}$ based upon the olefin. The reaction conditions which were employed for the oligomerization reaction included a reactor inlet temperature of 35° C. and a pressure of 700 psig. No conversion of butenes occurred during the first sixteen hours of this run. Furthermore, the temperature of the entire catalyst bed was 35° C. which was the temperature of the reactor inlet. Oligomerization is highly exothermic and even a low level of conversion would have been witnessed by some increase in the catalyst bed temperature. After sixteen hours the reactor inlet was increased to 70° C. An exotherm appeared on the catalyst bed and liquid oligomer product was formed. The oligomerization was allowed to proceed for an additional 194 hours, samples being taken and analyzed by gas chromatographic methods at various points during the reaction period. The results of these analyses are set forth in Table I below.

TABLE I

| HOURS | BUTENE CONVERSION % | SELECTIVITY $C_8$ = WT. % | $C_8$ = Isomer Distribution % | | |
|---|---|---|---|---|---|
| | | | N—OCTENE | METHYL HEPTENE | DIMETHYL HEXENE |
| 20 | 24 | 58 | 10 | 62 | 28 |
| 40 | 57.5 | 87 | 9 | 65 | 27 |
| 65 | 56 | 88 | 9 | 65 | 27 |
| 85 | 55.5 | 87 | 9 | 65 | 27 |
| 115 | 54.5 | 87 | 9 | 64 | 28 |
| 137 | 55 | 87 | 9 | 64 | 28 |
| 162 | 53.8 | 87 | 9 | 64 | 28 |
| 187 | 52.5 | 88 | 10 | 64 | 28 |
| 210 | 52.5 | 89 | 10 | 64 | 27 |

EXAMPLE V

In this example, the catalyst which was prepared according to the method set forth in Example II above in which the aluminum alkoxide activator was prepared by the addition of t-butyl alcohol and triethyl aluminum, was utilized to oligomerize a butene feed. The conditions which were employed in this oligomerization reaction were similar to those described in Example IV above, the feedstock, reaction pressure, and LSHV being identical. The inlet temperature was 70° C. for the entire run. The results of the analyses are set forth in Table II below:

TABLE II

| HOURS | BUTENE CONVERSION % | $C_8$ = Isomer Distribution % | | |
|---|---|---|---|---|
| | | N—OCTENE | METHYL HEPTENE | DIMETHYL HEXENE |
| 18 | 40 | 10 | 72 | 28 |
| 42 | 34 | 10 | 65 | 25 |
| 65 | 29.5 | 11 | 65 | 25 |
| 90 | 26 | 11 | 65 | 25 |
| 105 | 28 | 11 | 65 | 25 |

EXAMPLE VI

To contrast the relative activity and stability of catalysts which were prepared according to the present invention, another experiment was performed in which the oligomerization catalyst which was employed comprised a catalyst prepared according to Example III above. This catalyst did not contain an aluminum alkoxide activator but was prepared by treating the nickel containing base with aluminum chloride and diethyl aluminum chloride. The feedstock containing methyl-t-butyl ether contaminant was used. The run conditions were similar to those set forth in Example IV above. The catalyst was very active initially. The catalyst bed length was 14 in. and three hours after startup, the catalyst bed maximum temperature was 54° C. and 5½ in. from the inlet of the bed. However, four hours after startup the catalyst bed maximum temperature had moved down to 7 in. from the top, and during subsequent hours this movement continued. After ten hours, the entire bed was 35° C., the same as the inlet temperature. Thus, over a ten hour time span, the catalyst was completely deactivated. Loss of activity in the manner above (progressive, starting from the inlet) is indicative of deactivation due to poisoning by a feed contaminant. n-Butene conversion ceased before the end of the first twelve hour period. The results are set forth in Table III below:

TABLE III

| HOURS | BUTENE CONVERSION % | SELECTIVITY $C_8=$ WT. % | $C_8=$ Isomer Distribution % | | |
|---|---|---|---|---|---|
| | | | N—OCTENE | METHYL HEPTENE | DIMETHYL HEXENE |
| 6 | 79 | 60.1 | 8.0 | 64.6 | 27.4 |

We claim as our invention:

1. A catalytic composite for the oligomerization of olefins comprised of a catalytically effective amount of an activator comprising an aluminum alkoxy compound composited on a porous support containing a catalytically effective amount of an iron group metal compound, said catalyst prepared by the steps of impregnating a porous support with an aqueous solution of an iron group metal salt, calcining said impregnated support at a temperature in the range of from about 300° to 450° C., and contacting said calcined support with a solution comprised of an alkyl aluminum compound and an aluminum alkoxy compound.

2. The catalytic composite as set forth in claim 1 in which said iron group metal is present in said composite, on an elemental basis, in an amount in the range of from about 1% to about 20% by weight of said composite.

3. The catalytic composite as set forth in claim 1 in which said alkyl aluminum compound is present in said composite in a mol ratio to iron group metal in a range of from about 0.05:1 to about 6:1.

4. A catalytic composite as set forth in claim 1 in which said iron group metal is nickel.

5. A catalytic composite as set forth in claim 1 in which said iron group metal is cobalt.

6. A catalytic composite as set forth in claim 1 in which said alkyl aluminum compound comprises an alkyl aluminum halide.

7. A catalytic composite as set forth in claim 6 in which said alkyl aluminum halide is dimethyl aluminum chloride.

8. A catalytic composite as set forth in claim 6 in which said alkyl aluminum halide is diethyl aluminum chloride.

9. A catalytic composite as set forth in claim 1 in which said alkyl aluminum compound is triethyl aluminum.

10. A catalytic composite as set forth in claim 1 in which said aluminum alkoxy compound is tri-t-butoxy aluminum.

11. A catalytic composite as set forth in claim 1 in which said aluminum alkoxy compound is triethoxy aluminum.

12. A catalytic composite as set forth in claim 1 in which said aluminum alkoxy compound is tripropoxy aluminum.

13. A catalytic composite as set forth in claim 1 in which said porous support comprises alumina.

14. A catalytic composite as set forth in claim 1 in which said porous support comprises silica.

15. A catalytic composite as set forth in claim 1 in which said porous support comprises an aluminosilicate.

* * * * *